(12) United States Patent
Hately

(10) Patent No.: US 8,434,474 B2
(45) Date of Patent: May 7, 2013

(54) DISPENSING DEVICES

(75) Inventor: Graham Charles Hately, Norfolk (GB)

(73) Assignee: Consort Medical PLC, Hertfordshire (GB)

( * ) Notice: Subject to any disclaimer, the term of this patent is extended or adjusted under 35 U.S.C. 154(b) by 440 days.

(21) Appl. No.: 12/775,689

(22) Filed: May 7, 2010

(65) Prior Publication Data

US 2010/0282249 A1    Nov. 11, 2010

(30) Foreign Application Priority Data

May 11, 2009  (GB) ................................. 0908059.9

(51) Int. Cl.
  *A61M 11/00*  (2006.01)
  *B05B 17/00*  (2006.01)
  *B05B 7/00*   (2006.01)

(52) U.S. Cl.
  USPC ............ 128/200.23; 128/200.14; 128/200.15; 128/200.16; 128/200.17; 128/200.18; 128/200.19; 128/200.21; 128/200.22

(58) Field of Classification Search ........................ None
  See application file for complete search history.

(56) References Cited

U.S. PATENT DOCUMENTS

| | | | |
|---|---|---|---|
| 6,119,853 A | 9/2000 | Garrill et al. | |
| 6,179,118 B1 | 1/2001 | Garrill et al. | |
| 6,250,468 B1 * | 6/2001 | Huchel | 206/446 |
| 2007/0181120 A1 | 8/2007 | Wright et al. | |
| 2007/0235469 A1 | 10/2007 | Bacon | |
| 2007/0284383 A1 | 12/2007 | Wright et al. | |
| 2008/0017192 A1 | 1/2008 | Southby et al. | |
| 2008/0017193 A1 * | 1/2008 | Jones et al. | 128/200.23 |
| 2008/0135575 A1 | 6/2008 | Ingram et al. | |

FOREIGN PATENT DOCUMENTS

| | | |
|---|---|---|
| EP | 1 859 829 A1 | 11/2007 |
| GB | 1335304 A | 10/1973 |
| WO | 00/37336 A1 | 6/2000 |
| WO | 01/98175 | 12/2001 |
| WO | 03/080161 | 10/2003 |
| WO | 2005/051467 A1 | 6/2005 |
| WO | 2007/132217 | 11/2007 |
| WO | 2009/061276 | 5/2009 |

OTHER PUBLICATIONS

Combined Search and Examination for GB 0908059.9 dated Sep. 1, 2009 (5 pages).
European Registered Community Design Registration Nos. 000740147-001 to 005 filed Jun. 11, 2007.
U.S. Appl. No. 29/293,781, filed Dec. 11, 2007 of inventor Simon Ingram.
Extended European Search Report for Application No. EP 10 157 711.2 dated Jul. 27, 2010.

* cited by examiner

*Primary Examiner* — Melanie Hand
*Assistant Examiner* — Joshua Lee
(74) *Attorney, Agent, or Firm* — Smith, Gambrell and Russell, LLP

(57) ABSTRACT

Dispensing apparatus for delivering metered doses of product from a pressurized dispensing container, having a housing for receiving, in use, the pressurized dispensing container, and an outlet through which, in use, metered doses of product from the pressurized dispensing container can be dispensed. The housing has an aperture via which the pressurized dispensing container can be inserted into the housing. The dispensing apparatus is at least partially enclosed by a shrink wrapped film, the shrink wrapped film including an opening which is:
  (a) at least partly aligned with the aperture of the housing; and
  (b) dimensioned so as to allow, in use, said pressurized dispensing container to pass through the opening in order to be inserted into the housing via the aperture.

22 Claims, 10 Drawing Sheets

DISPENSING DEVICES

This invention relates to a dispensing device, in particular a metered dose aerosol inhaler device, comprising an improved packaging arrangement.

It is common for a manufacturer of dispensing apparatus for use with a pressurised dispensing container to provide the dispensing apparatus to an intermediate party for the intermediate party to install the pressurised dispensing container into the dispensing apparatus to form a dispenser assembly. The dispenser assembly may then be supplied to the end user.

It is important to minimise cosmetic damage during the steps of shipping the dispensing apparatus to the intermediate party, installing the pressurised dispensing container and onward shipping to the end user.

In the past this has been achieved by producing bulk transit packaging in which multiple units of a dispensing apparatus were shipped to the intermediate party. One of the functions of the transit packaging is to protect the apparatus and another is to prevent components becoming detached from the apparatus. On receipt by the intermediate party, the transit packaging is removed and discarded prior to installation of the pressurised dispensing container into the dispensing apparatus. This transit packaging is not easily recycled and this results in large amounts of waste.

Before shipping the product to the end user the intermediate party may package the complete dispensing assembly in secondary packaging such as a cardboard box outer. Bowl feeding apparatus may be used to insert the dispensing assembly into the secondary packaging.

It is also important that each party can be confident that the dispensing apparatus has not been tampered with since being dispatched by the previous party.

Previously, it was common for the manufacturer of the dispensing apparatus to provide some form of tamper-evident means to the dispensing apparatus prior to supplying to the intermediate party. The intermediate party would then remove the tamper-evident means prior to installing the pressurised dispensing container. Once the pressurised dispenser was installed the intermediate party would install another new tamper evident means to the dispenser assembly before shipping to the consumer.

This results in a considerable quantity of energy and resources being allocated to ensuring that the product is not tampered with before reaching the consumer.

Against this background, according to the present invention there is provided a dispensing apparatus for delivering metered doses of product from a pressurised dispensing container, the dispensing apparatus comprising a housing for receiving, in use, said pressurised dispensing container, and an outlet through which, in use, metered doses of product from said pressurised dispensing container can be dispensed, the housing comprising an aperture via which said pressurised dispensing container can be inserted into said housing, wherein the dispensing apparatus is at least partially enclosed by a shrink wrapped film, the shrink wrapped film including an opening which is:

(a) at least partly aligned with the aperture of the housing; and (b) dimensioned so as to allow, in use, said pressurised dispensing container to pass through the opening in order to be inserted into the housing via the aperture.

Advantageously, the shrink wrap film protects the apparatus during transit and prevents components being detached.

Thus, either no separate transit packaging is required or a simpler, less expensive and less wasteful form of transit packaging can be used.

Another advantage is that the apparatus is particularly suitable for bowl feeding, for example, into secondary packaging.

Also advantageously, recipients of the dispensing apparatus can be confident that the covered parts of the apparatus have not been tampered with prior to removal of the shrink wrapped film.

Advantageously, the opening in the shrink wrapped film allows a purchaser of the apparatus to insert a pressurised dispensing container into the dispensing apparatus without damaging or altering the shrink wrapped film.

Preferably, the dispensing apparatus further comprises a mouthpiece.

More preferably, the shrink wrapped film at least partially encloses the mouthpiece in order to retain the mouthpiece.

Advantageously, a user may be confident that the mouthpiece has not been tampered with prior to removal of the film.

Preferably, the shrink wrapped film is a shrink wrapped plastic film.

Preferably, the shrink wrapped film comprises a line of weakness or a weakened portion to allow the shrink wrapped to be removed by a user.

Preferably, the dispensing apparatus further comprises a dose counter mechanism.

According to another aspect of the present invention there is provided a dispensing assembly comprising the dispensing apparatus being at least partially enclosed by a shrink wrapped film and a pressurised dispensing container received in the housing of the dispensing apparatus.

According to another aspect of the present invention there is provided a method of manufacturing and packaging a dispensing apparatus of the type comprising a housing for receiving, in use, a pressurised dispensing container, and an outlet through which, in use, metered doses of product from said pressurised dispensing container can be dispensed, the housing comprising an aperture via which said pressurised dispensing container can be inserted into said housing, the method comprising the steps of:

a) manufacturing said dispensing apparatus; and b) at least partially enclosing said dispensing apparatus in a shrink wrap film.

Preferably, the method further comprises the step of:

c) inserting a pressurised dispensing container into said dispensing apparatus whist the shrink wrap film is still at least partially enclosing the dispensing apparatus.

Preferably, the dispensing apparatus comprises a mouthpiece and the shrink wrap film of step b) at least partially encloses the mouthpiece to retain the mouthpiece during subsequent transport of the dispensing apparatus.

Preferably, the method additionally comprises the step of forming a line of weakness or weakened portion in the shrink wrap film.

The dispensing device may be a pharmaceutical dispensing device, such as, for example, a pulmonary, nasal, or sublingual delivery device. A preferred use of the dispensing device is as a pharmaceutical metered dose aerosol inhaler device. The term pharmaceutical, as used herein, is intended to encompass any pharmaceutical, compound, composition, medicament, agent or product which can be delivered or administered to a human being or animal, for example pharmaceuticals, drugs, biological and medicinal products. Examples include antiallergics, analgesics, bronchodilators, antihistamines, therapeutic proteins and peptides, antitussives, anginal preparations, antibiotics, anti-inflammatory preparations, hormones, or sulfonamides, such as, for example, a vasoconstrictive amine, an enzyme, an alkaloid, or a steroid, including combinations of two or more thereof. In particular, examples include isoproterenol [alpha-(isopropylaminomethyl) protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, ipratropium bromide and salbutamol, flunisolide, colchicine, pirbuterol, beclomethasone, orciprenaline, fentanyl, and diamorphine, streptomycin, penicillin, procaine penicillin, tetracycline, chlorotetracycline and hydroxytetracycline, adrenocorticotropic hormone and adrenocortical hormones, such as cortisone, hydrocortisone, hydrocortisone acetate and prednisolone, insulin, cromolyn sodium, and mometasone, including combinations of two or more thereof.

The pharmaceutical may be used as either the free base or as one or more salts conventional in the art, such as, for example, acetate, benzenesulphonate, benzoate, bircarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate, (embonate), pantothenate, phosphate, diphosphate, polygalacturonate, salicylate, stearate, subacetate, succinate, sulphate, tannate, tartrate, and triethiodide, including combinations of two or more thereof. Cationic salts may also be used, for example the alkali metals, e.g. Na and K, and ammonium salts and salts of amines known in the art to be pharmaceutically acceptable, for example glycine, ethylene diamine, choline, diethanolamine, triethanolamine, octadecylamine, diethylamine, triethylamine, 1-amino-2-propanol-amino-2-(hydroxymethyl)propane-1,3-diol, and 1-(3,4-dihydroxyphenyl)-2 isopropylaminoethanol.

The pharmaceutical will typically be one which is suitable for inhalation and may be provided in any suitable form for this purpose, for example as a solution or powder suspension in a solvent or carrier liquid, for example ethanol, or isopropyl alcohol. Typical propellants are HFA134a, HFA227 and di-methyl ether.

The pharmaceutical may, for example, be one which is suitable for the treatment of asthma. Examples include salbutamol, beclomethasone, salmeterol, fluticasone, formoterol, terbutaline, sodium chromoglycate, budesonide and flunisolide, and physiologically acceptable salts (for example salbutamol sulphate, salmeterol xinafoate, fluticasone propionate, beclomethasone dipropionate, and terbutaline sulphate), solvates and esters, including combinations of two or more thereof. Individual isomers such as, for example, R-salbutamol, may also be used. As will be appreciated, the pharmaceutical may comprise of one or more active ingredients, an example of which is flutiform, and may optionally be provided together with a suitable carrier, for example a liquid carrier. One or more surfactants may be included if desired.

Rigid components of the dispensing apparatus may be formed from, for example, from polyester, nylon, acetal or similar.

In order that the invention may be fully disclosed, embodiments will now be described, by way of example, with reference to the accompanying drawings, in which:—

For the purposes of illustrating the present invention it will be described with reference to its application to a dispensing device of the type described in detail in EP1859829. The contents of EP1859829 are hereby incorporated by reference. However, it should be understood that the invention is not limited to a dispensing devices of the specific design described below and in EP1859829 but finds application with other dispensing devices, most preferably dispensing devices in the form of metered dose aerosol inhaler devices which comprise a dispensing apparatus in which is inserted a pressurised dispensing container having a metering valve therein.

Figure 1:
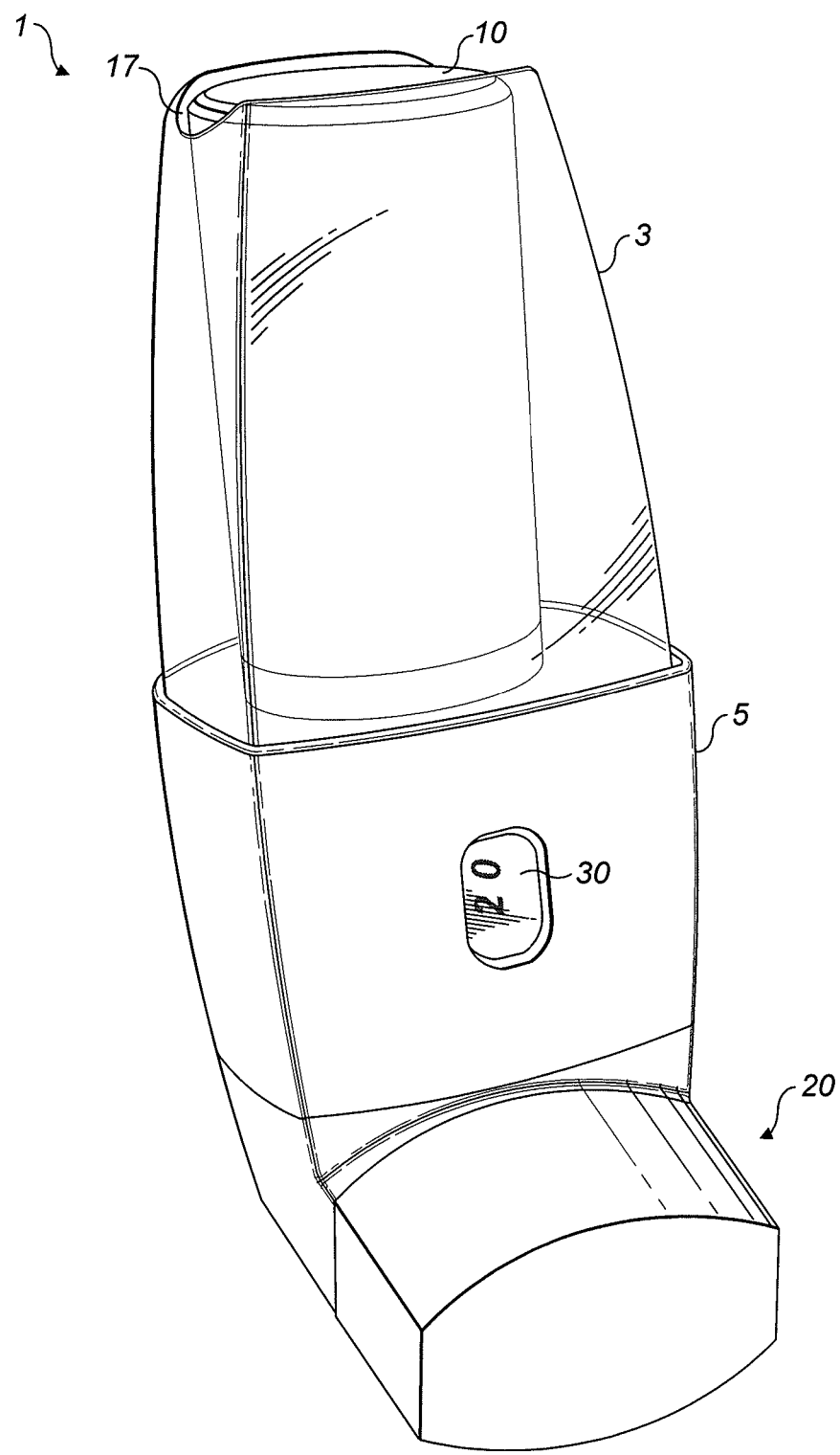
FIG. 1 is a perspective view of a dispensing apparatus with a pressurised dispensing container inserted therein.
Figure 2:
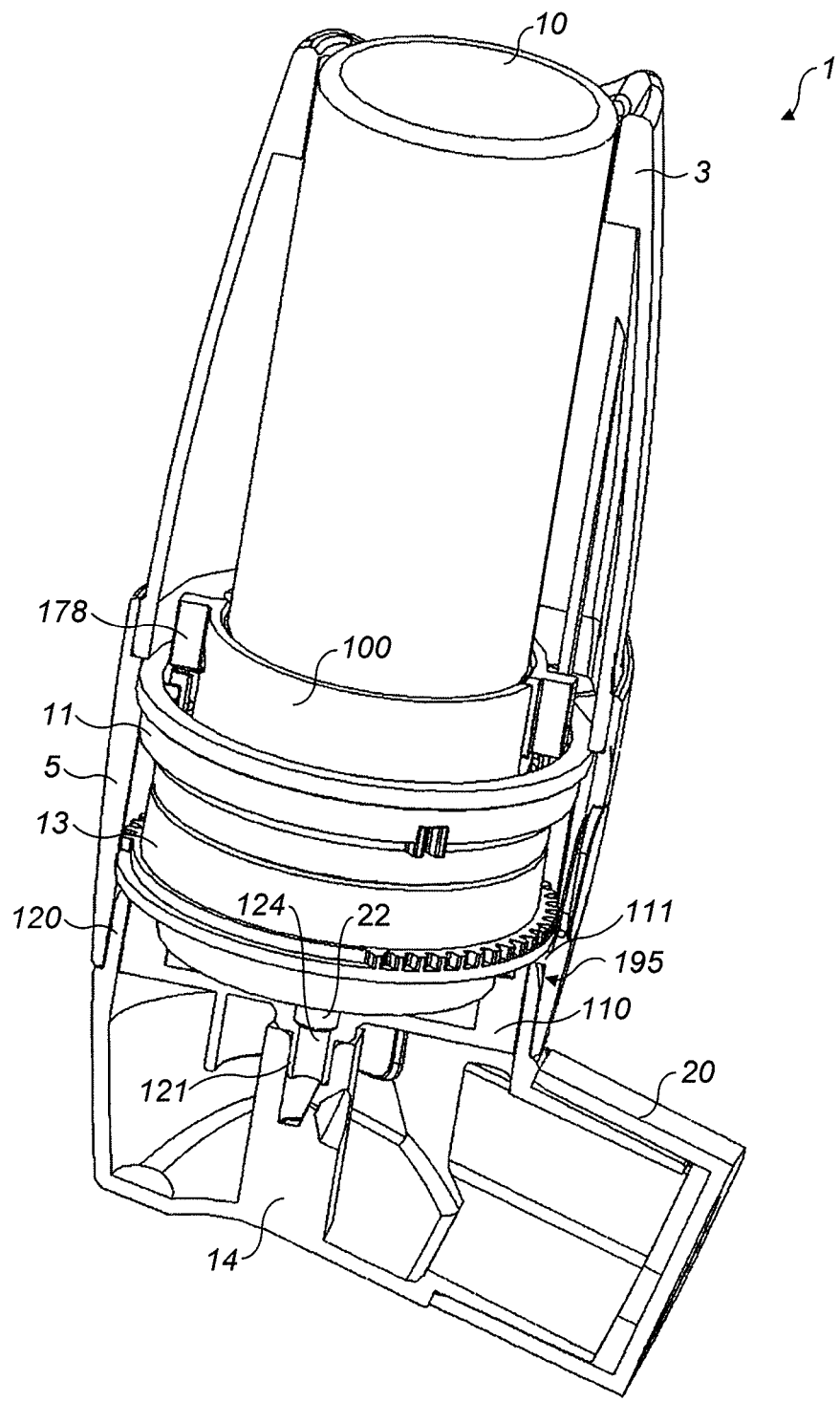
FIG. 2 is a cross-sectional view of the apparatus of FIG. 1.
Figure 8:
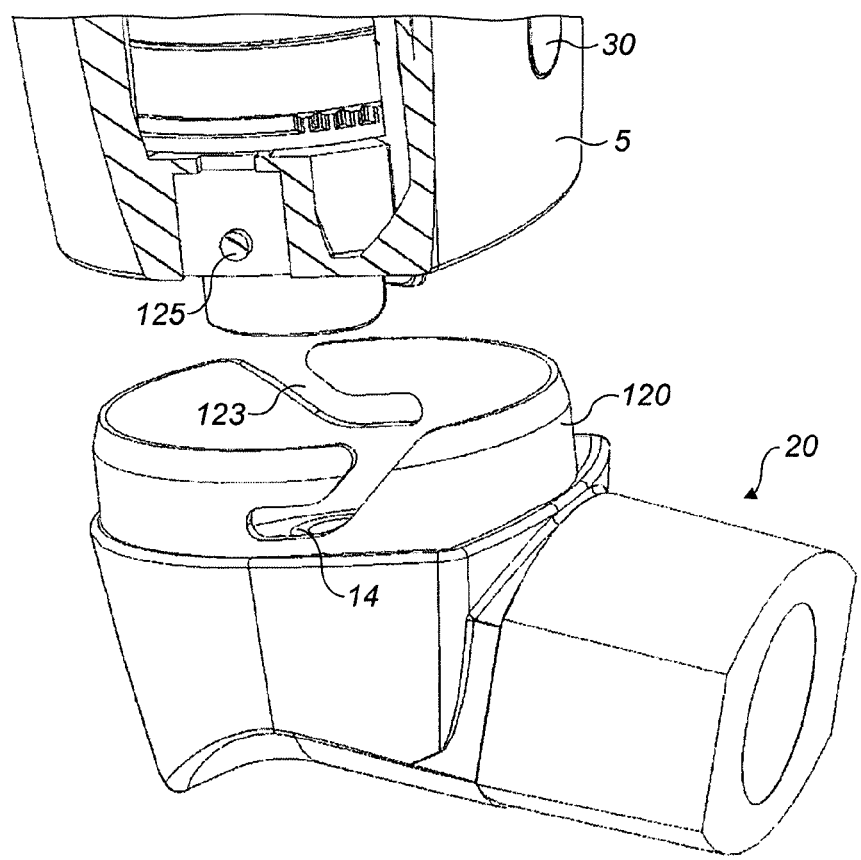
FIG. 8 is a perspective view of the dispensing apparatus of FIG. 1 with the mouthpiece detached and some parts shown in cross-section.
Figure 9:
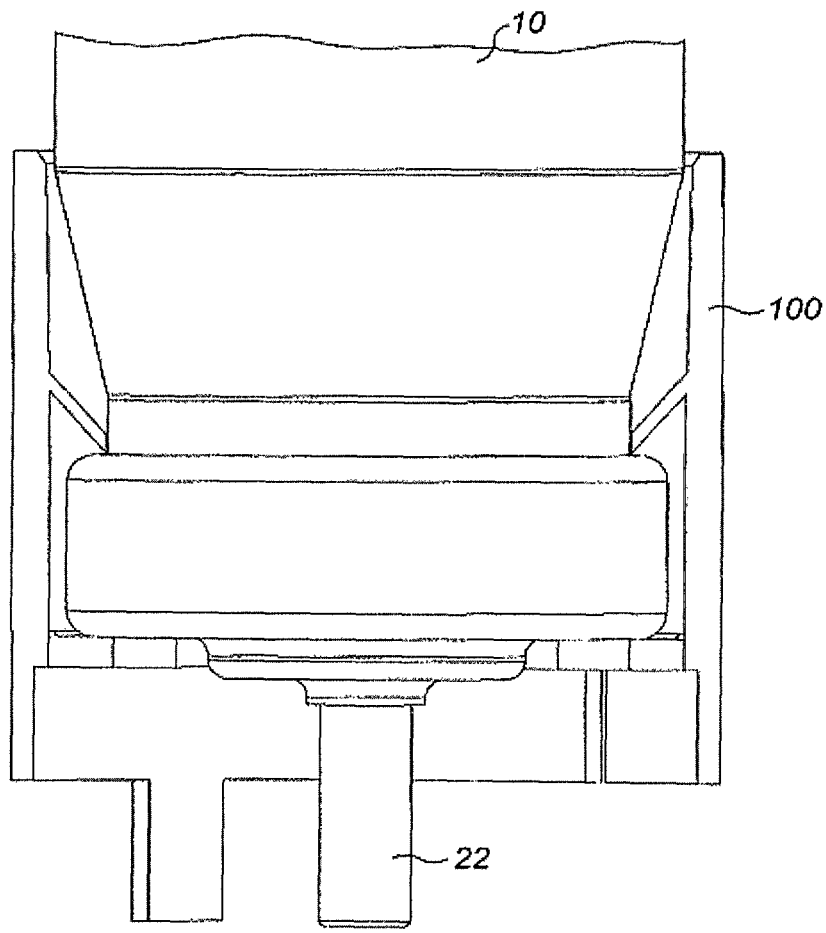
FIG. 9 is a schematic view of part of the apparatus of FIG. 1 with some parts omitted for clarity.

FIG. 1 shows a dispensing apparatus, indicated generally at 1, having a upper body 3, a lower body 5 and a detachable mouthpiece 20 shown in FIG. 8. A dust cap may be used to cover the mouthpiece 20 when the apparatus is not in use. As shown in FIG. 2, the dispensing apparatus is also provided with first and second number rings 11,13, a cog 12 and a sleeve 100. In use the apparatus receives a pressurised dispensing container 10 to form a dispensing assembly or device.

The lower body 5 is open at its upper end. The lower body 5 houses the cog 12 and the first and second number rings 11, 13. As shown in more detail in FIG. 3, the number rings 11, 13 rest upon internal projections 111 of the main body 5. Such internal projections 111 provide up-facing surfaces upon which the second number ring 13 may rest and rotate, during use. The first number ring 11 rests and rotates, during use, on top of the second number ring 13. The cog 12 is rotatably mounted within the main body 5 on a cylindrical portion 112 and interacts with both first and second number rings 11, 13. As can be seen, the axis of rotation of the cog 12 is offset from the axes of the numbered rings 11, 13 but parallel thereto so that the cog 12 can interact with both number rings 11, 13 which are housed in the substantially cylindrical part of the lower body 5 without impeding axial movement of the container 10.

The lower body 5 is provided at a lower end thereof with an axial protrusion 121 integral with the lower body 5. The axial protrusion 121 comprises a hollow elongate portion into which the valve stem 22 of the container 10 can be received as a relatively tight interference fit. The hollow portion is provided with a narrowed constriction against which the valve stem 22 can abut when the dispensing apparatus is actuated. The hollow portion forms a conduit 124 that is in fluid communication with the outlet of the valve stem of the pressurised dispensing container when the container is inserted into the apparatus. The axial protrusion 121 protrudes from the lower end of the lower body 5 as shown in FIG. 2. The axial protrusion 121 provides protection for the valve stem when the mouthpiece 20 has been removed and also directs dispensed product into the removable mouthpiece 20. In particular with the mouthpiece 20 removed the valve stem 22 is not easily accessed as it is recessed relative to the distal end of the protrusion 121. This significantly reduces the chance that the container 10 could be actuated by direct pressure being applied to the end of the valve stem 22 which might circumvent the dose counter mechanism.

The lower body 5 and upper body 3 are connectable together using co-operating formations which are push-fit together as shown in FIG. 2.

The detachable mouthpiece 20 is attached to the main body 5 by means of a bayonet fitting. As shown in FIGS. 2 and 8 the mouthpiece 20 is provided with an upstanding rim 120 in which are formed two opposed recesses 123 of roughly an L-shape configuration. The main body 5 comprises a circumferential recess 195 which receives the rim 120 when the two pieces are coupled together. At opposed points of the circumferential recess 195 the lower body 5 is provided with retaining lugs 125 which pass along the recesses 123 of the mouthpiece. Thus the mouthpiece may be coupled to the lower body 5 by locating the lugs 125 relative to the upper end of the recesses and then twisting the lower body 5 relative to the mouthpiece 20 whilst applying a compressive axial force to the two components. This results in the lugs 125 riding along the recesses resulting in the two components being firmly connected. Accordingly, it is very simple to change the mouthpiece of the dispensing apparatus, if desired or remove the mouthpiece for washing. The mouthpiece 20 is also provided with a spray block 14 for receipt of the axial protrusion 121. The spray block 14 comprises a conduit having an upper end which receives the axial protrusion 121 and a lower end which comprises a spray outlet directed towards the outlet of the mouthpiece 20. The spray outlet may be provided with a suitably dimensioned orifice or spray pattern block as known in the art to produce an atomised spray of product on dispensation.

Figure 7:
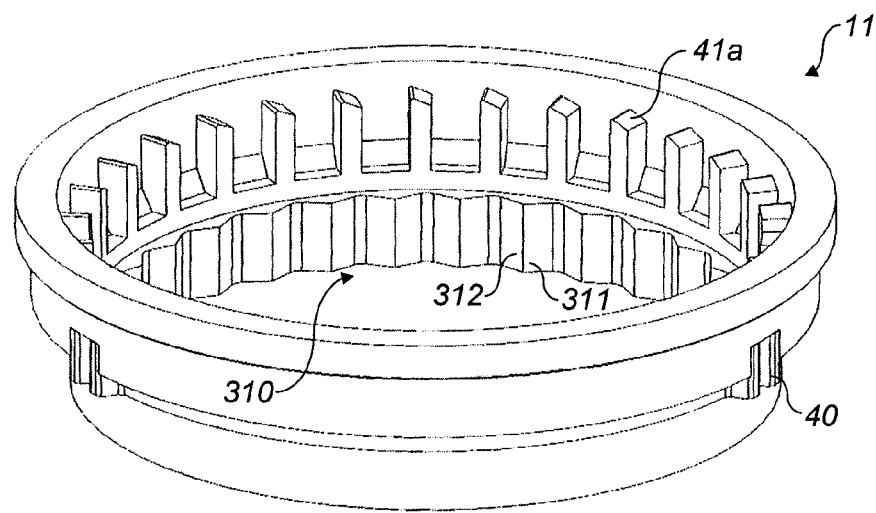
FIG. 7 is a perspective view of a first number ring having two different diameter portions, forming part of the dispensing apparatus of FIG. 1.

The first number ring 11 is provided with an upper row of angled abutment surfaces 41a located on a larger diameter portion of that number ring as shown in FIG. 7. A lower set of angled abutment surfaces are formed on a smaller diameter portion of the ring in the form of a series of inwardly directed projections 310 having a triangular cross-section when viewed from above. The projections 310 are arranged around the circumference of the lower portion of the ring 11 so as to form a series of interspersed peaks and troughs. Each projection 310 comprises two faces 311, 312 on either side of the peak. Preferably, the faces 311, 312 are arranged symmetrically about the peak. The faces 311 and 312 form angled abutment surfaces which engage the outward projection 304 of the tension arm 300 in use as will be described below.

The first number ring 11 comprises at least one notch 40 positioned on the outer edge thereof. The first number ring 11 is also provided with a set of numbering (not shown in the drawings) from 0 to 9 for each notch 40, so that after the ninth actuation of the apparatus 1, the notch 40 is in position to interact with the cog 12. In a preferred embodiment, the number ring 11 will have three notches 40 and, so, will have three sets of numbering from 0 to 9.

Figure 4:
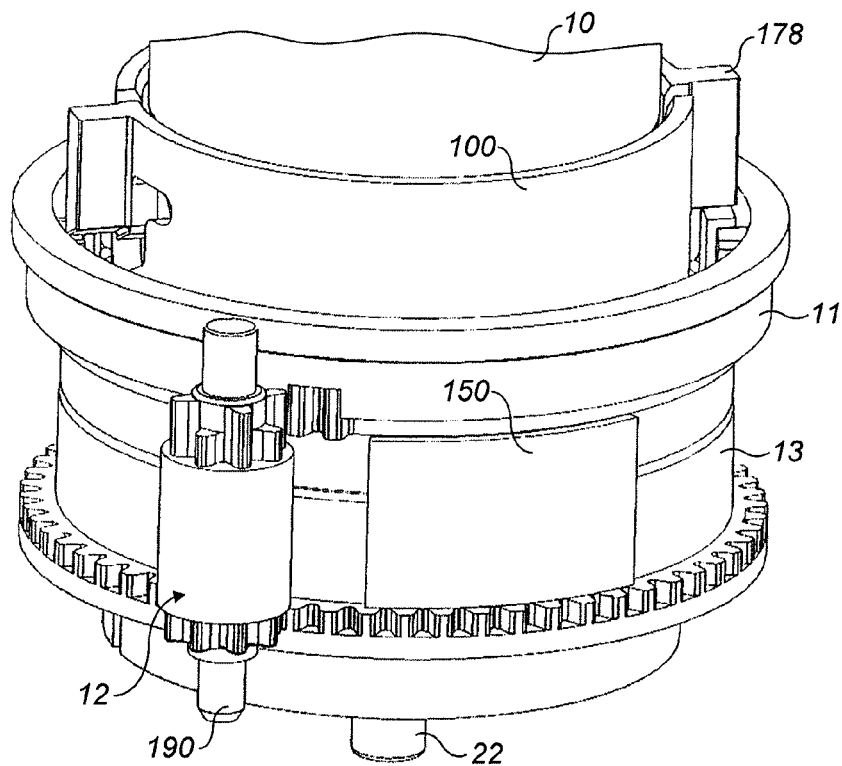
FIG. 4 is a perspective view of first and second number rings and the cog forming part of the dispensing apparatus of FIG. 1.

The second number ring 13 is provided with an extended portion 150, as shown in FIG. 4, which is positioned to enable covering of the markings on the first number ring 11 when a container locatable in the housing is empty. Advantageously, the extended portion 150 provides a clear indication to a user that the dispensing apparatus has provided its full-quota of dispensations.

Figure 3:
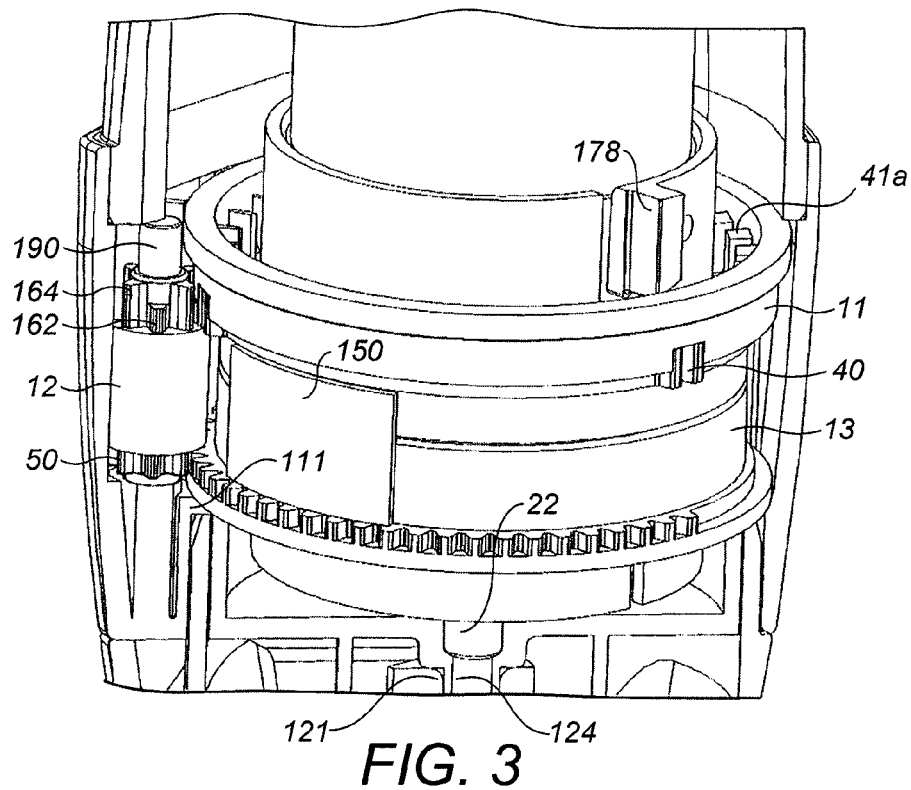
FIG. 3 is a perspective view of various internal features of the dispensing apparatus of FIG. 1.
Figure 5:
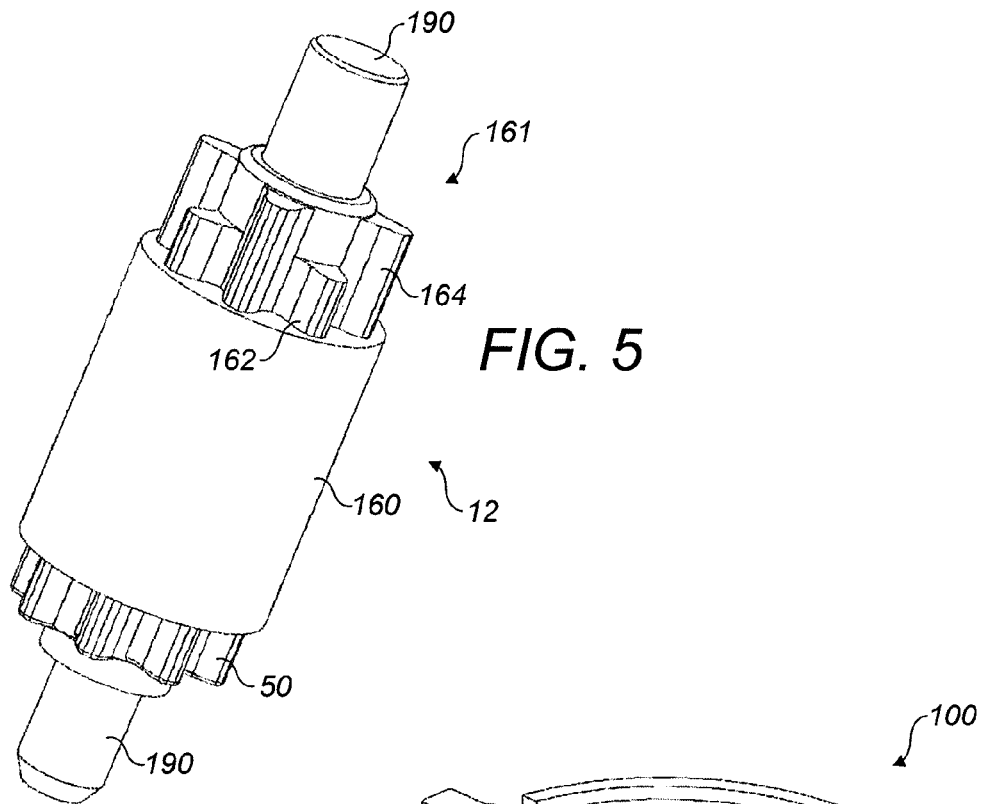
FIG. 5 is a perspective view of a cog forming part of the dispensing apparatus of FIG. 1.

The cog 12, as shown in FIG. 5 in particular, is provided with one or more teeth separated by a non-toothed, cylindrical, spacer 160. A first end 161 of the cog 12 includes four teeth 162 of reduced height and four teeth 164 of full height which in use interact with the first annular member 11. The full height teeth 164 extend from the spacer 160 to the distal face of the first end 161 of the cog 12. The teeth 50 at a second end of the cog 12 are all full height and these teeth in use interact with the second annular member 13. The four teeth 162 having reduced height are, typically, half the height of the full height teeth 164. Most preferably, the reduced height teeth 162 and full height teeth 164 are arranged alternately around the circumference of the cog 12. The cog 12 is provided with upper and lower axial projections 190 which allow the cog 12 to be rotationally mounted in recesses formed in the lower body 5 as shown in FIG. 3.

Figure 6:
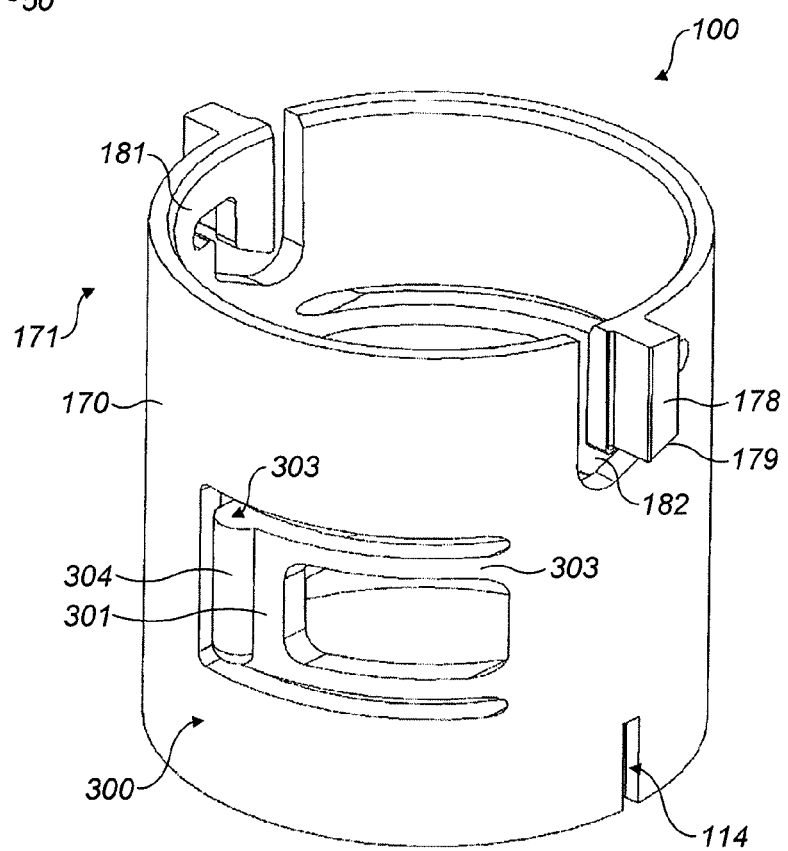
FIG. 6 is a perspective view of a sleeve forming part of the dispensing apparatus of FIG. 1.

As shown in FIGS. 2 and 6, the sleeve 100 comprises an open-ended cylinder 170 having an upper end 171 which can receive the container 10 to be located in the dispensing apparatus 1 and a lower end 172 which has a reduced diameter opening 173 through which the valve stem 22 of the container 10, located within the sleeve 100 may protrude from but through which the body of the container 10 cannot pass. The sleeve 100 is provided with two sets of formations on its exterior surface. The sets of formations are arranged diametrically opposite one another (only one set of formations is shown in FIG. 6). Each set of formations comprises first, second and third formations. The first formation is provided at the lower end 172 in the form of notches 114. The second formation is provided above the notches 114 in the form of a tension arm 300. The tension arm 300 comprises a cantilevered portion 301 which is fixed to the sleeve 100 at a hinge point 302. Preferably, the tension arm 300 is provided in a single moulding as part of the sleeve 100 in which case the hinge point 302 marks the junction between the body of the sleeve 100 and the start of the cantilevered portion 301 of the tension arm 300. A distal end 303 of the tension arm 300 is provided with an outwardly directed projection 304. It can be seen from FIG. 6 that the cantilevered tension arm 300 is able to accommodate flexure in a direction perpendicular to flexure of the cantilevered projection 178. That is, the outwardly directed projections 304 of the tension arm 300 can flex substantially radially inwards when pressure is applied to the projections in a radially inward direction. It will be appreciated that the shape of the container 10 must accommodate inward flexure of the tension arms 300. It is therefore preferable that the position of the tension arms 300 be located to coincide with the neck of the container 10 where it narrows to meet the ferrule of the metering valve, thereby forming an undercut. Alternatively, the walls of the container 10 may have formed in them depressions to accommodate inward flexure of the tensions arms 300. The third formation is provided at the upper end 171 in the form of a cantilevered projection 178. The cantilevered projection 178 comprises an elongated portion 180 having an angled abutment surface 179 on its lower, distal end. The elongated portion 180 of the cantilevered projection 178 is axially aligned with the projection 175. The elongated portion 180 is joined to the cylindrical body of the sleeve 100 at a hinge point 181. A void space 182 is formed around the elongated portion 180 to accommodate movement of the cantilevered projection 179 in use as will be described below.

The lower body 5 is provided with a clear portion 30, or one or more apertures 30 through which portions provided with markings of the number rings 11, 13 are visible. The upper body 3 is transparent to allow a user to easily see the type of container 10 located in the apparatus 1.

The opening in the upper body 3 is sized such that the sleeve 100 cannot pass therethrough but so that the container 10 is able to pass through.

In use, the internal components of the apparatus, such as the cog 5, the sleeve 100 and the number rings 11, 13 can be loaded into position within the apparatus 1 by separating the upper body 3 from the lower body 5. The cog, number rings and sleeve 100 can be inserted into the opening of the lower body 5. The internal projections 110 of the lower body 5 are received slidingly in the notches 114 of the sleeve 100 with the effect that the sleeve 100 is fixed rotationally relative to the lower body 5. The sleeve 100 is arranged to pass through the central holes/apertures of the number rings 11, 13. The upper body 3 is then attached to the lower body 5. The connection between the upper body 3 and lower body 5 may be designed to prevent easy further detachment of the two parts to thereby provide a tamper-resistant means of enclosing the container 10.

The pressurised dispensing container 10 can now be passed through the hole in the upper body 3 to be received in the sleeve 100. The valve stem 22 of the pressurised dispensing container 10 is received in the opening of the conduit 124 of the axial protrusion 121 as a relatively tight interference push-fit. When loaded, the number rings 11,13 are located around the container 10 as shown in FIG. 3.

In the inserted position the upper end of the container 10 protrudes upwardly through the hole in the upper body 3 as shown in FIG. 1. Preferably, the container 10 only protrudes slightly above the level of the upper body 3. In the illustrated embodiment scallops 17 are provided in the upper edge of the upper body 3 and the container 10 protrudes above the level of the scallops but does not protrude above the highest part of the upper edge. The depth of the scallops 17 allows a user to depress the container 10 sufficiently to actuate the container's valve but reduces the area of the container 10 that can be gripped by the fingers of anyone attempting to remove the container 10 from the apparatus 1. Thus the amount of pulling force that can be applied to the container 10 is not enough to overcome the friction produced by the interference fit between the valve stem 22 and the conduit 124. Also, the fact that the container 10 does not protrude above the highest part of the upper edge helps to prevent accidental actuation of the apparatus when carried in the pocket. Advantageously, this mechanism of retaining the container 10 within the body portion can be used on its own without the need to provide an additional non-return feature.

The device 1 is actuated as described in detail in EP1859829, the contents of which are hereby incorporated by reference.

Figure 10:
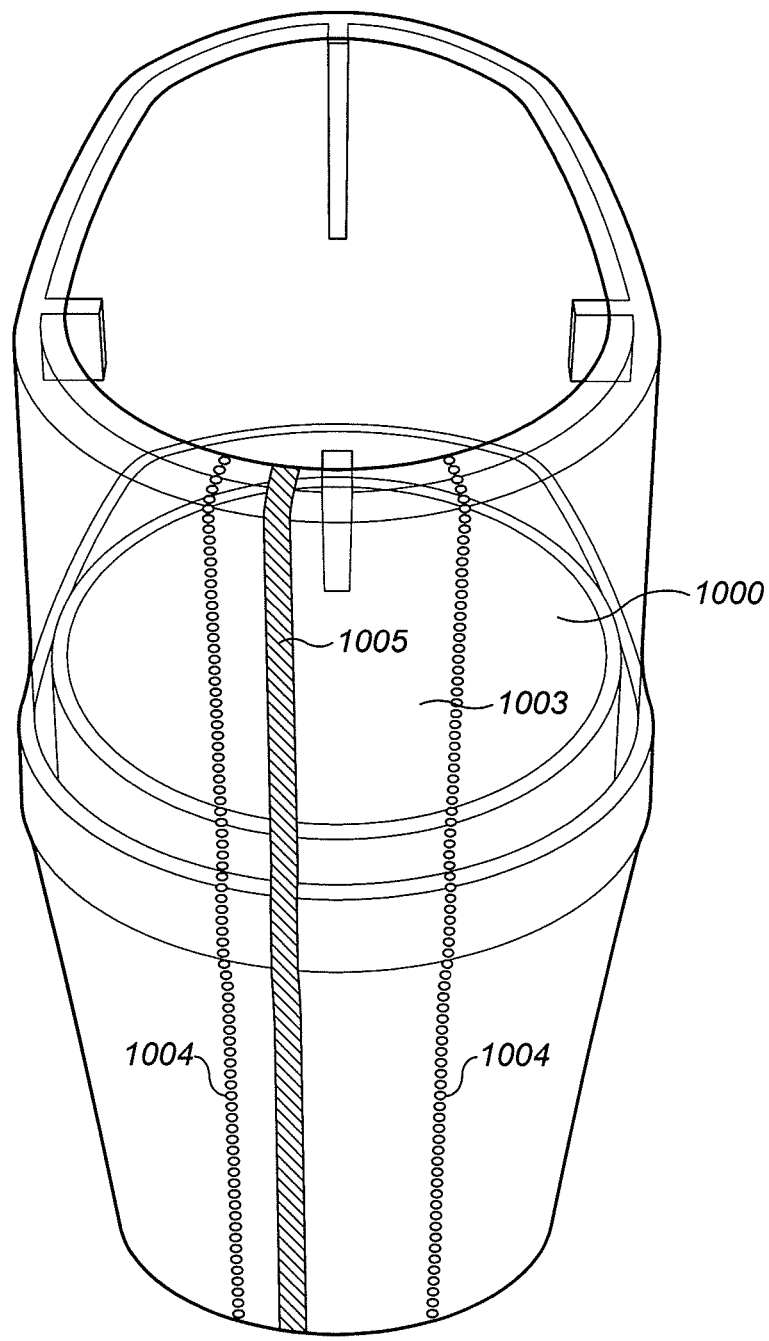
FIG. 10 is a schematic rear view of a dispensing apparatus partially enclosed by a shrink wrapped film according to the invention.

According to the present inventive improvement, as shown in FIG. 10, the dispensing apparatus 1 is provided with a shrink wrapped film 1000 to surround at least a portion of the dispensing apparatus 1, prior to insertion of the pressurised dispensing container 10.

Figure 11:
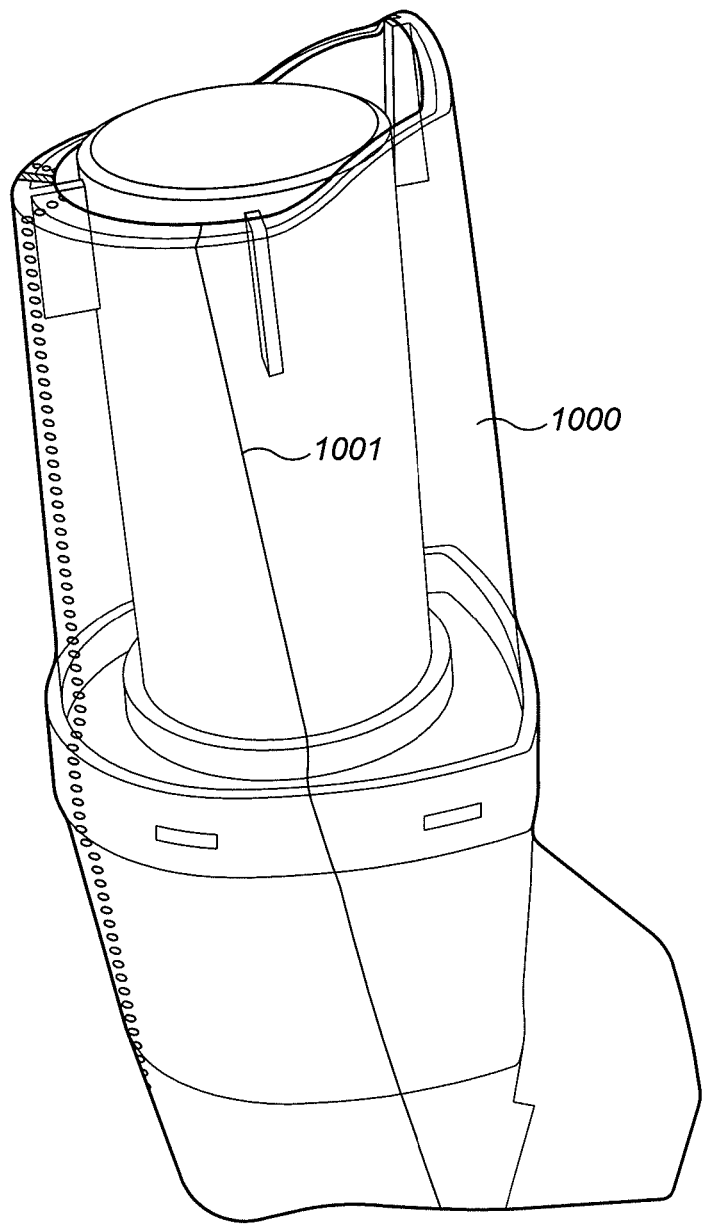
FIG. 11 is a schematic side view of a dispensing assembly comprising a dispensing apparatus and a pressurised dispensing container wherein the dispensing apparatus is partially enclosed by a shrink wrapped film according to the invention.
Figure 12:
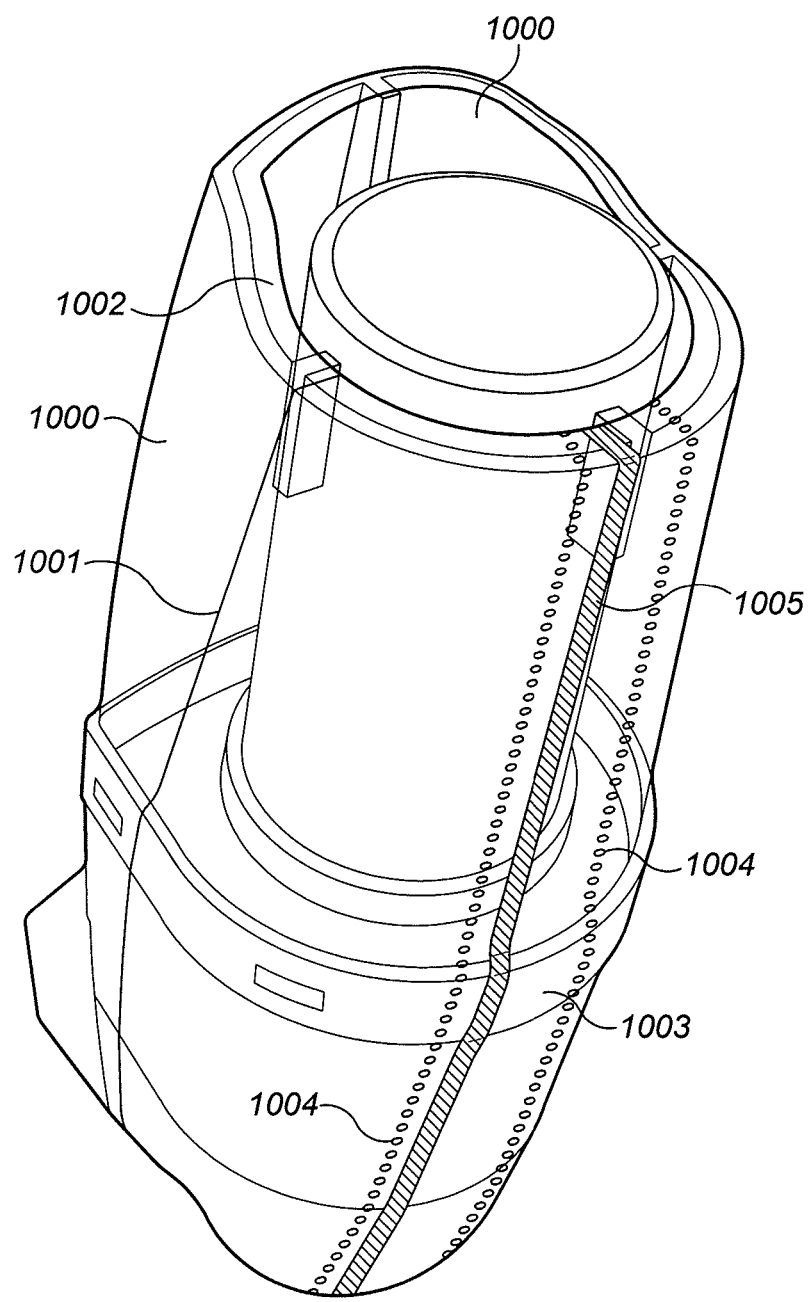
FIG. 12 is a schematic view of the dispensing assembly of FIG. 11 showing a line of weakness in the film.
Figure 13:
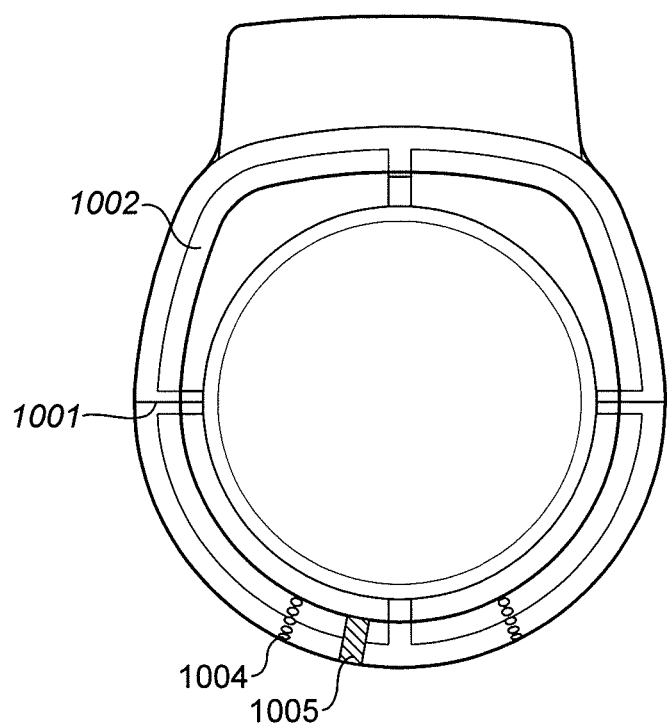
FIG. 13 is a schematic top view of the dispensing assembly of FIGS. 11 and 12.

FIGS. 11, 12 and 13 show not only the dispensing apparatus 1 and shrink wrapped film 1000 but also the pressurised dispensing container 10 which is received into the dispensing apparatus 1 when in use.

The film 1000 covers the external surface of the apparatus 1 except for an opening 1010 which aligns substantially with, and is slightly smaller than, the aperture in the housing of the dispensing apparatus, as shown, in particular, in FIG. 12.

The shrink wrapped film 1000 extends up and slightly over the upper rim of the upper body so as to comprise a substantially annular portion 1002 which surrounds the opening such that the annular portion 1002 covers a portion of the aperture in the dispensing apparatus 1. The opening in the film 1000 is of sufficient size to allow the pressurised dispensing container 10 to pass therethrough, in order to be received into the dispensing apparatus 1.

Suitable shrink wrapped films include films formed from Polyvinyl Chloride (PVC), Polyethylene Terephthalate (PET), Oriented Polystyrene (OPS) and Polylactic Acid (PLA) and are available from, for example, CCL Decorative Sleeves of Kings Lynn, United Kingdom.

The shrink wrapped film 1000 may be formed from one or more independent film components. Seams 1001 may, therefore, result at each location where two or more film components are joined to form the shrink wrapped film 1000.

Once the dispensing apparatus 1 has had the film 1000 applied thereto, it may be shipped to a manufacturer who will fit the pressurised dispensing containers 10. At this stage, the pressurised dispensing container 10 may be inserted into the aperture of the housing via the opening in the film. Since the opening is of sufficient dimensions to allow the pressurised dispensing container to pass therethrough, the film need not be damaged during the process of inserting the pressurised dispensing container into the aperture. The relative dimensions of the opening and aperture are clear from, in particular, FIG. 12.

Once applied to the apparatus, the shrink wrapped film 1000 is not sufficiently elastic to be removed from the dispensing apparatus 1 merely by deforming the film 1000. Instead, in order to remove the film 1000 from the dispensing apparatus 1 it is necessary to break the film. A line of weakness or a weakened portion 1003 is provided to allow the film to be broken and hence removed from the dispensing apparatus 1.

Removal of the film would usually be performed by the end user (patient) prior to first use of the dispensing apparatus for dispensing the medicament from the pressurised dispensing container.

In the examples illustrated in FIGS. 10 and 12, the line of weakness 1003 comprises two parallel lines of perforations 1004 extending from the top to the bottom of the film. Between the parallel lines of perforations 1004 is located a ribbon 1005 attached to the inner surface of the film 1000. A portion of the ribbon 1005 extends beyond the dimensions of the film 1000 such that the portion is accessible to the user. To remove the film 1000 the user pulls the accessible portion of the ribbon 1005 which exerts a force on the film 1000. When sufficient force is applied, the film 1000 will tear along the two parallel perforated lines 1004. Hence the film will be broken and this will allow the film 1000 to be removed from the apparatus 1.

While FIGS. 10 and 12 show the line of weakness 1003 in the film 1000 to be vertical and adjacent to the rear of the apparatus 1 it is within the scope of the invention, as would readily be appreciated by the skilled person, for the line of weakness to be located at any position on the film and in any orientation.

As is clear from FIG. 11, the shrink wrap film 1000 covers the mouthpiece 20, such that the mouthpiece 20 is inaccessible and not removable when the shrink wrapped film 1000 is in place.

In addition, the shrink wrap film 1000 covers those elements of the dose counter which might otherwise be externally accessible with respect to the housing.

Covering the dispensing apparatus 1 with the film 1000 provides for several advantages. One such advantage is that, assuming the film remains in place, the supplier of the pressurised dispensing container can be confident that the covered elements have not been tampered with prior to insertion of the pressurised dispensing container. Another advantage is that the end user can be confident that the covered elements have not been tampered with prior to removal of the film (which the user would remove prior to first use of the apparatus).

The invention claimed is:

1. Dispensing apparatus for delivering metered doses of product from a pressurised dispensing container, the dispensing apparatus comprising a housing for receiving, in use, said pressurised dispensing container, and an outlet through which, in use, metered doses of product from said pressurised dispensing container can be dispensed, the housing comprising an aperture via which said pressurised dispensing container can be inserted into said housing,
   wherein the dispensing apparatus is at least partially enclosed by a shrink wrapped film, the shrink wrapped film including an opening which is:
   (a) at least partly aligned with the aperture of the housing; and
   (b) dimensioned so as to allow, in use, said pressurised dispensing container to pass through the opening in order to be inserted into the housing via the aperture.

2. The dispensing apparatus of claim 1 wherein the dispensing apparatus further comprises a mouthpiece.

3. The dispensing apparatus of claim 2 wherein the shrink wrapped film at least partially encloses the mouthpiece in order to retain the mouthpiece in assembled attachment with the dispensing apparatus.

4. The dispensing apparatus of claim 1 wherein the shrink wrapped film is a shrink wrapped plastic film.

5. The dispensing apparatus of claim 1 wherein the shrink wrapped film comprises a line of weakness or a weakened portion to allow the shrink wrapped film to be removed by a user.

6. The dispensing apparatus of claim 1 wherein the dispensing apparatus further comprises a dose counter mechanism.

7. A dispensing assembly comprising the dispensing apparatus of claim 1 being at least partially enclosed by a shrink wrapped film and a pressurised dispensing container received in the housing of the dispensing apparatus.

8. The dispensing apparatus of claim 2 wherein the dispensing apparatus further comprises a dose counter mechanism.

9. A dispensing assembly comprising the dispensing apparatus of claim 2 being at least partially enclosed by a shrink wrapped film and a pressurised dispensing container received in the housing of the dispensing apparatus.

10. The dispensing apparatus of claim 1 wherein the shrink wrapped film at least partially encloses the dispensing apparatus over an axial length of the dispensing apparatus, and the shrink wrapped film has a perimeter that varies over a length of the dispensing apparatus in cross-sections taken along the axial length of the dispensing apparatus.

11. The dispensing apparatus of claim 1 wherein the shrink wrapped film includes an annular portion that covers a portion of the dispensing apparatus aperture.

12. The dispensing apparatus of claim 1 wherein the shrink wrapped film is arranged on the dispensing apparatus so as to cover a dose level viewing region of said housing.

13. The dispensing apparatus of claim 1 wherein the shrink wrapped film is arranged on the dispensing apparatus so as to cover an entire external surface of said housing but for the aperture of said housing.

14. A method of manufacturing and packaging a dispensing apparatus of the type comprising a housing for receiving, in use, a pressurised dispensing container, and an outlet through which, in use, metered doses of product from said pressurised dispensing container can be dispensed, the housing comprising an aperture via which said pressurised dispensing container can be inserted into said housing, the method comprising the steps of:
   a) manufacturing said dispensing apparatus; and
   b) at least partially enclosing said dispensing apparatus in a shrink wrap film, the shrink wrap film including an opening which is at least partly aligned with the aperture of the housing and dimensioned so as to allow, in use, a pressurised dispensing container to pass through the opening in order to be inserted into the housing via the aperture.

15. The method of claim 14 wherein the dispensing apparatus comprises a mouthpiece and the shrink wrap film of step b) at least partially encloses the mouthpiece to retain the mouthpiece in assembled attachment with the dispensing apparatus during subsequent transport of the dispensing apparatus.

16. The method of claim 14 additionally comprising the step of forming a line of weakness or weakened portion in the shrink wrap film.

17. The method of claim 14 wherein the step of enclosing the dispensing apparatus in the shrink wrap film includes arranging the shrink-wrap film on the dispensing apparatus such that it at least partially encloses the dispensing apparatus over an axial length of the dispensing apparatus, and such that it has a perimeter that varies over a length of the dispensing apparatus in cross-sections taken along the axial length of the dispensing apparatus.

18. The dispensing apparatus of claim 14 wherein the step of enclosing the dispensing apparatus in the shrink wrap film includes arranging the shrink-wrap film on the dispensing apparatus such that an annular portion of the shrink wrapped film covers a portion of the dispensing apparatus aperture.

19. A method of manufacturing and packaging a dispensing apparatus of the type comprising a housing for receiving, in use, a pressurised dispensing container, and an outlet through which, in use, metered doses of product from said pressurised dispensing container can be dispensed, the housing comprising an aperture via which said pressurised dispensing container can be inserted into said housing, the method comprising the steps of:
   a) manufacturing said dispensing apparatus;
   b) at least partially enclosing said dispensing apparatus in a shrink wrap film, the shrink wrap film including an opening which is at least partly aligned with the aperture of the housing and dimensioned so as to allow, in use, a pressurized dispensing container to pass through the opening in order to be inserted into the housing via the aperture; and
   c) inserting a pressurised dispensing container into said dispensing apparatus whilst the shrink wrap film is still at least partially enclosing the dispensing apparatus.

20. The method of claim 19 wherein the dispensing apparatus comprises a mouthpiece and the shrink wrap film of step b) at least partially encloses the mouthpiece to retain the mouthpiece in assembled attachment with the dispensing apparatus during subsequent transport of the dispensing apparatus.

21. The method of claim 19 additionally comprising the step of forming a line of weakness or weakened portion in the shrink wrap film.

22. The method of claim 15 additionally comprising the step of forming a line of weakness or weakened portion in the shrink wrap film.

\* \* \* \* \*